United States Patent [19]
Denton

[11] Patent Number: 6,112,743
[45] Date of Patent: Sep. 5, 2000

[54] CONNECTOR FOR SYRINGE AND ATOMIZER AND THE LIKE

[75] Inventor: Marshall T. Denton, Salt Lake City, Utah

[73] Assignee: Wolfe Tory Medical, Inc., Salt Lake City, Utah

[21] Appl. No.: 09/148,927

[22] Filed: Sep. 4, 1998

[51] Int. Cl.$^7$ .................................................. A61M 25/00
[52] U.S. Cl. ................. 128/200.14; 128/202.27; 128/200.23; 604/187
[58] Field of Search ...................... 128/200.22, 202.27, 128/203.23, 207.18, 200.14; 604/187

[56] References Cited

U.S. PATENT DOCUMENTS

| | | |
|---|---|---|
| D. 333,000 | 2/1993 | Good et al. . |
| D. 340,185 | 10/1993 | Martone . |
| D. 344,231 | 2/1994 | Gagnon . |
| 3,459,177 | 8/1969 | Deuschle .............................. 604/187 |
| 3,628,523 | 12/1971 | Pirtle .................................. 128/202.27 |
| 4,620,847 | 11/1986 | Shishov et al. ..................... 604/187 |
| 4,767,416 | 8/1988 | Wolf et al. ......................... 128/200.14 |
| 5,176,415 | 1/1993 | Choksi ................................ 128/202.27 |
| 5,490,630 | 2/1996 | Hecker . |
| 5,511,538 | 4/1996 | Haber et al. . |
| 5,759,178 | 6/1998 | Wells ...................................... 604/187 |
| 5,927,975 | 7/1999 | Esrock ...................................... 433/80 |

OTHER PUBLICATIONS

Official Gazette, p. 2224, Apr. 15, 1997.
"Meeting the Challenge . . .", *Valois Pharm.*, pp. 1–12.

*Primary Examiner*—John G. Weiss
*Assistant Examiner*—V. Srivastava
*Attorney, Agent, or Firm*—Trask Britt

[57] ABSTRACT

A coupling to connect a commercially available syringe to a commercially available atomizer. In one embodiment the coupling is generally cylindrical, has a through-bore, and has a length dimension to generally minimize spacing between the syringe and atomizer to enable dexterity and ease of use of the assembly. One end of the coupling has an interference fit interface with an atomizer, and the other end provides a demountable LUER-LOCK connection with a syringe. A second embodiment provides a LUER-LOCK connector at one end of a tube of a convenient length. A second end of the tube is adhesively joined to connecting structure to secure an atomizer nozzle. The tube may contain a deformable wire to define any curvilinear shape in the coupling body between the syringe and nozzle.

14 Claims, 1 Drawing Sheet

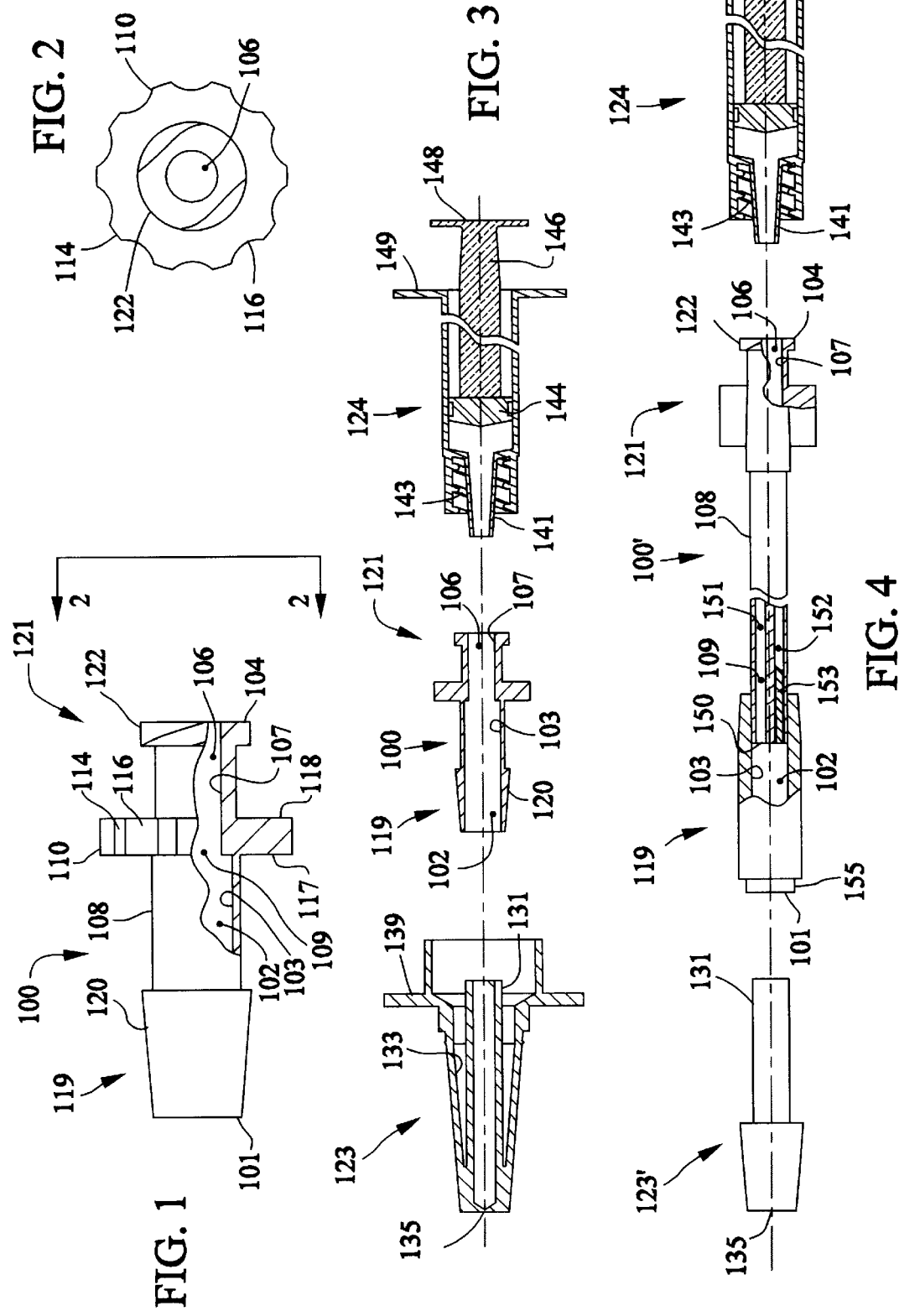

CONNECTOR FOR SYRINGE AND ATOMIZER AND THE LIKE

TECHNICAL FIELD

This invention relates to devices for dispensing fluids in a controlled amount and dispersed form. It is particularly directed to medical devices which create therapeutic mists suitable for use in applications such as medication of sinus passages and oral surgery.

BACKGROUND

Syringes and atomizing nozzles are generally known. Controlled amounts of various fluids may be easily dispensed utilizing a syringe. Mass produced and relatively inexpensive, syringes are capable of generating fairly high fluid pressure (up to about 120 pounds per square inch "(p.s.i.)") with relative ease. They are easily and quickly loaded with a variety of medical fluid compositions, and may be reloaded. Syringes are available having structure adapted to connect the syringe to another component. One such connector structure includes a LUER-LOCK joint located at the discharge end of the syringe.

Atomizing nozzles have been widely used to disperse fluids into mists including droplets of various small sizes. Such nozzles generally require a pressurized source of fluids. Discharged fluids generally form mists including many small diameter droplets. Such mists have improved properties of fluid dispersion compared to fewer and larger drops; dispensing fluids more uniformly and over a correspondingly larger area. Medicine applied as a mist thereby covers a larger area in a thin layer. Capillary attraction to the treated surface operates upon the thin layer of medicine, whereby the medication is less inclined to be affected by gravity and drip from the treatment area.

Atomizer assemblies are known, including an atomizer nozzle, a reservoir of fluid, and a pressurizing mechanism such as a plunger. Such devices are generally capable of only a single use, as the reservoir is not easily refillable by drawing fluids in reverse through the nozzle. Multiple mist discharges are feasible due to the reservoir, but only a single medication can be dispensed by a conventional assembly. Components forming atomizer assemblies are generally fastened together by way of a permanent interference fit, or a bonded joint, thereby frustrating the ability to reload the fluid reservoir. Commercially available atomizer nozzles do not provide structure that can interface directly with a syringe to form a syringe-atomizer assembly.

DISCLOSURE OF THE INVENTION

The present invention provides an apparatus for connecting a syringe to an atomizer or atomizing nozzle. In particular, a coupling adapter is disclosed for connecting a commercially available syringe to a commercially available atomizer. The coupling provides a compact interface between two incompatible connector types. It also allows commercially available components to be connected without requiring any retooling of the respective components. The combination of a syringe and atomizer forms a convenient and easily manipulated fluid application device for dispensing therapeutic fluids in the form of a mist. A mist possesses improved properties, for example, in treating nasal cavities, compared to bulb "eye dropper" technology. Topical medical treatments may be applied nasally without the requirement of tipping the patient's head back, or inverting his or her head from an upright position. A surgical application might be to load a syringe with a topical anesthetic, then apply it as a mist to a patient's throat prior to intubation. A sore throat may be treated in a like manner. Application of a mist provides assurance that coverage will be distributed over a large area, and also that the medicinal fluids will be less likely to then immediately drip from the treated area. The invention provides a space saving multipurpose misting apparatus. A demountable syringe provides the ability to select between medications. Inventory volume may be reduced by removing the need to have pre-loaded atomizers dedicated to each medication.

The invention discloses a coupling for securing a syringe to an atomizer. The coupling has first and second ends; each end carrying connecting structure, wherein the first end is connectable to an atomizer, and the second end of the coupling is demountably connectable to a syringe. The coupling may further include a deformable body located between the first and second ends. Such a body has at least one through-bore, providing fluid communication between the atomizer and syringe. One or more additional bores through the body may carry a deformable wire to impart an arbitrary, generally curvilinear, shape to the body. Such wires may be adhesively secured. A body may further include a rigidly attached grasping structure including a cylindrical disk with a knurled outer circumferential surface. An axis of the disk is located approximately coaxial an axis oriented in a length direction of the coupling and passing through the center of the coupling body. Such a grasping structure may find use to apply force to the coupling when creating an assembly, particularly when connecting a coupling to an atomizer. The connection between the coupling and the atomizer may include any joining method, including an adhesive bond or an interference fit. One method of providing a mating interference fit includes forcibly inserting a cylindrical shaft of an atomizer into a cylindrical bore located in the first end of the coupling. Of course, for an interference fit between coupling and shaft, the cylindrical bore of the coupling has an internal dimension less than an external dimension of the cylindrical shaft of the atomizer. The length of engagement between the cylindrical shaft of the atomizer and the cylindrical bore of the coupling may be determined by a shoulder formed by a reduction in dimension in the bore of the coupling. A LUER-LOCK fitting forms an exemplary demountable connection between the syringe and coupling.

BRIEF DESCRIPTION OF THE FIGURES

In the drawings, which illustrate what is currently regarded as the best mode for carrying out the invention and in which like reference numerals refer to like parts in different views or embodiments:

FIG. 1 is a plan view in partial cross-section of a coupling according to the invention.

FIG. 2 is an end view of the coupling of FIG. 1, looking in the direction of arrows 2—2 of FIG. 1.

FIG. 3 is an exploded, plan view in cross-section of an assembly according to the invention which includes an atomizer, a coupling, and a syringe having a LUER-LOCK adaptor.

FIG. 4 is an exploded, plan view in partial cross-section of a preferred embodiment of an assembly according to the invention which includes an atomizer, a coupling, and a LUER-LOCK syringe.

BEST MODE OF THE INVENTION

One embodiment of coupling 100 is shown in FIG. 1. A first or distal end 101 has an interior distal bore 102 formed by approximately cylindrical bore surface 103. A second or proximal end 104 of coupling 100 houses an interior proximal bore 106 formed by approximately cylindrical bore surface 107. Distal end 101 and proximal end 104 are spaced apart in a lengthwise direction by body 108. The body 108 includes a generally cylindrical hollow structure. Distal and proximal bores 102 and 106 are in open fluid communication, forming through-bore 109 interior to body 108.

An optional grasping structure 110 is located between the distal and proximal ends. As best shown by FIG. 2, grasping structure 110 includes a cylindrical disk carrying spaced protuberances 114 and dishes 116 on an outer circumference. These protuberances 114 and dishes 116 provide a grippable, knurled circumferential surface that enables torque transmission to the coupling body. Other surface configurations, such as a hexagonal bolt-head pattern are within contemplation. Axially directed force on the coupling 100 may be transmitted through distal shoulder 117 or proximal shoulder 118, or by pressing directly on proximal end 104. Distal end 101 carries a first connecting structure 119 including distal bore 102 and, optionally, a generally conic tapered mating surface 120. Proximal end 104 carries a second connecting structure, generally 121, such as a male LUER-LOCK thread 122 and proximal bore 106.

Coupling 100 can be made from a variety of materials and manufacturing methods. It is currently preferred to injection mold couplings from polypropylene, although other moldable materials can be substituted. Couplings can also be cast or machined, although injection molding is currently preferred. While bores 102 and 106 are of approximately uniform diameter along a lengthwise dimension, each diameter may taper to provide mold release draft, or may vary for other reasons.

As best shown by FIG. 3, coupling 100 forms an interface between structure such as atomizer 123 and syringe 124. Atomizer 123 and syringe 124 are components that are readily commercially available. The presently preferred atomizer is commercially available from Valois Pharm of Le Neubourg, France. The atomizer 123 includes a cylindrical shaft 131 which fits in snug sealing engagement with cylindrical surface 103 of distal bore 102. The atomizer 123 further includes a conical interior surface 133 which fits in sealing interference fit engagement with optional tapered mating surface 120 on distal end 101 of coupling 100. An atomizer 123 also generally includes a nozzle orifice 135 and finger support gripping structure 139.

The coupling 100 is advantageously assembled in semipermanent fashion to an atomizer 123 by forcibly sliding atomizer cylindrical shaft 131 axially into distal bore 102. The coupling 100 may be rotated relative to atomizer 123 during the insertion process. Axially directed forces may be applied to grasping structure proximal shoulder 118, or directly to proximal end 104 of the coupling. It is currently preferred to locate a retractable pin concentric to the atomizer cylindrical shaft 131 during assembly. An interference fit is created on assembly; first between the atomizer cylindrical shaft 131 and coupling bore 102, and second between atomizer tapered surface 133 and coupling mating surface 120. It is within contemplation that the second interference fit, between atomizer tapered surface 133 and coupling mating surface 120, could be eliminated as the seal from the first interference fit is adequate. The length of engagement between the atomizer cylindrical shaft 131 and coupling 100 can be limited by a stop or shoulder formed by a reduction in internal diameter between distal and proximal bores 102 and 106. An interference fit between the components is adequate to maintain engagement between the coupling 100 and atomizer 123 during normal use. However, a permanent mounting may also be achieved by use of various common techniques, including solvent or acoustic welding and adhesive compounds.

A syringe 124 has a LUER-LOCK connection including a tapered stem 141 and female threaded end 143. The syringe also generally includes a plunger seal 144, a plunger shaft 146 having a thumb actuation end 148, and finger support flanges 149. In an assembly, the syringe 124 is detachably mounted to the proximal end 104 of coupling 100 by the LUER-LOCK connection. Male thread 122 interfaces with female threaded end 143. Twisting the components in a tightening direction draws tapered stem 141 into proximal bore 106. The proximal bore 106 is sized to fit to a diameter of tapered stem 141 in releasable, sealing engagement. In an assembly, syringe 124 may be activated by thumb actuation end 148 in combination with either finger support structure 139 of the atomizer, or syringe finger support flanges 149. The demountable and resealable property of the LUER-LOCK joint allows the syringe to be reloaded as required.

A preferred embodiment of an assembly including an atomizer, a coupling, and a syringe is shown in FIG. 4. In this embodiment, the assembly is generally similar to that of FIG. 3, and like structure is denoted with like numerals. The coupling, generally 100', has a distal end 101 and a proximal end 104. A distal end 150 of body 108 carries a first connecting structure, generally 119, including an interior distal bore 102 formed by approximately cylindrical bore surface 103. In this presently preferred embodiment, a portion of the distal end 150 of body 108 is adhesively bonded interior distal bore 102, forming a lap joint with a portion of bore surface 103. As illustrated, body 108 includes a flexible multi-lumen tube having a second connecting structure 121 including a LUER-LOCK connector associated with a proximal end. Proximal end 104 of coupling 100' houses a proximal bore 106 formed by approximately cylindrical bore surface 107. Distal bore 102, proximal bore 106, and interior bore 151 are in open fluid communication, forming through-bore 109. Interior bore 152 is included in the illustrated preferred embodiment, although its presence is optional. A deformable wire 153 is preferably glued or otherwise adhered or associated with interior bore 152, thereby providing means to define a deformable, adjustable curvilinear shape in body 108. As illustrated, coupling distal end 101 includes a necked-down shoulder region 155.

Atomizer 123' shown in FIG. 4 is a reduced version of atomizer 123, shown in FIG. 3. Prototypes were made by scribing around a circumference, through the exterior conic section, to form two pieces and discarding the section including the finger support structure. Atomizers may be made in a more conventional manner, for example, by injection molding. The resulting atomizer has a cylindrical shaft 131, and an orifice 135. A truncated portion of surface 133 remains (not shown in FIG. 4). As in the previously described embodiment, the coupling 100' is advantageously assembled in semi-permanent fashion to an atomizer 123' by forcibly sliding atomizer cylindrical shaft 131 axially into distal bore 102. An interference fit is created on assembly between the atomizer cylindrical shaft 131 and coupling bore 102. Coupling necked-down shoulder region 155 fits in plug-fit engagement with the remaining portion of surface 133. Necked-down shoulder region 155 is not required, and may be eliminated. An interference fit between the shaft 131 and distal bore 102 is adequate to maintain engagement between the coupling 100' and atomizer 123' during normal use. However, a permanent mounting may also be achieved by use of various common techniques, including solvent or acoustic welding and adhesive compounds.

In an assembly, the syringe 124 is detachably mounted to the proximal end 104 of coupling 100' by a LUER-LOCK connection including bore 106, thread 122, threaded end 143, and tapered stem 141. Male thread 122 interfaces with female threaded end 143. Twisting the components in a tightening direction draws tapered stem 141 into proximal bore 106. Proximal bore 106 is sized to fit to a diameter of tapered stem 141 in releasable sealing engagement.

Coupling 100' can be made from a variety of materials and manufacturing methods. It is currently preferred to make coupling body 108 of any useful or convenient length from a commercially available polyvinylchloride (PVC) multi-lumen tube having a LUER-LOCK connection integral one end. The first connecting structure 119 is preferably made from polycarbonate, although other moldable materials can be substituted. While bores 102 and 106 are of approximately uniform diameter along a length dimension, each diameter may taper to provide mold release draft, or may vary for other reasons. Interference fits may be replaced by adhesive joints.

Although the invention has been described with regard to certain preferred embodiments, the scope of the invention is to be defined by the appended claims.

What is claimed is:

1. A syringe and fluid-atomizer coupling comprising:
    a body having at least one through-bore and a deformable wire, physically associated with said body, to maintain a shape in said body upon deformation of said deformable wire to said shape;
        a first connecting structure associated with a first end of said body, said first connecting structure configured and arranged for securing a commercially available fluid-atomizer to said body by forming a connection upon assembly with said fluid-atomizer; and
        a second connecting structure associated with a second end of said body, said second connecting structure configured and arranged for demountably securing a syringe to said body.

2. The syringe and fluid-atomizer coupling of claim 1, wherein said body further comprises a rigidly attached grasping structure comprising a cylindrical disk with a knurled outer circumferential surface, said disk having an axis located approximately coaxial an axis oriented in a lengthwise direction and passing through the center of said body.

3. The syringe and fluid-atomizer coupling of claim 1, wherein said first connecting structure for securing said fluid atomizer to said body is configured and arranged to provide a mating interference fit with structure associated with said fluid atomizer.

4. The syringe and fluid-atomizer coupling of claim 1, wherein said second connecting structure for demountably securing said syringe to said body is a LUER-LOCK fitting.

5. The syringe and fluid-atomizer coupling of claim 1, wherein said first connecting structure is adhesively bonded to a first end of said body.

6. A syringe and atomizer assembly comprising:
    a coupling comprising:
        a body having:
            at least one axially oriented through-bore,
            a deformable wire, physically associated with said body, to maintain a shape in said body upon deformation of said deformable wire while maintaining the through-bore's integrity,
        a distal end carrying a first connecting means for securing an atomizer to said hollow body by forming a connection upon assembly with said atomizer;
        a proximal end carrying a second connecting means for securing a syringe to said hollow body;
    a syringe demountably secured to said proximal end of said coupling; and
    an atomizer rigidly secured to said distal end of said coupling.

7. An apparatus for securing a syringe to an atomizer having a cylindrical shaft, said apparatus comprising:
    a coupling comprising:
        a body having a distal end and a proximal end;
            said distal end having a cylindrical bore,
            said proximal end carrying means for connecting a syringe to said body,
        a through-bore providing fluid communication between said distal and proximal ends,
            a deformable wire, physically associated with said body, to maintain a shape in said body upon deformation of said deformable wire while retaining the through-bore's integrity, and
        said cylindrical bore being configured and arranged to form a connection upon assembly in a mating fit with said cylindrical shaft of said atomizer.

8. The apparatus of claim 7, wherein said cylindrical bore of said coupling has an internal dimension less than an external dimension of said cylindrical shaft of said atomizer.

9. The apparatus of claim 8, wherein said cylindrical bore of said coupling is structured and arranged to receive said cylindrical shaft by way of forcible insertion of said cylindrical shaft into said cylindrical bore.

10. The apparatus of claim 9, wherein the length of engagement between said cylindrical shaft of said atomizer and said cylindrical bore of said coupling is determined by a shoulder formed by a reduction in dimension in said cylindrical bore of said coupling.

11. An apparatus for securing a syringe to an atomizer, said apparatus comprising:
    a coupling having first and second ends and a wire wherein,
        said first end of said coupling carries coupling structure adapted to form a connection to structure associated with said atomizer upon assembly of said coupling structure with said structure associated with said-atomizer,
        said second end of said coupling is demountably connectable to said syringe, and said wire, physically associated with said coupling, to maintain said coupling's shape upon deformation of said wire while retaining a lumen through said coupling.

12. The apparatus of claim 11, wherein said first end of said coupling is adapted for connection to said atomizer by an interference fit.

13. The apparatus of claim 11, wherein said coupling is adapted for connection to said atomizer by an adhesive bond.

14. The apparatus of claim 12, wherein:
    said first end of said coupling comprises a cylindrical bore, said cylindrical bore being adapted for assembly to said atomizer by forcible insertion of structure associated with said atomizer into said cylindrical bore.

* * * * *

UNITED STATES PATENT AND TRADEMARK OFFICE
CERTIFICATE OF CORRECTION

PATENT NO.        : 6,112,743
APPLICATION NO.   : 09/148927
DATED             : September 5, 2000
INVENTOR(S)       : Marshall T. Denton Page 1 of 1

It is certified that error appears in the above-identified patent and that said Letters Patent is hereby corrected as shown below:

In the specification:
COLUMN 1, LINE 18, change ""(p.s.i.")" to --("p.s.i.")--

In the claims:
CLAIMS 3, COLUMN 5, LINES 52-53, change "fluid atomizer" to --fluid-atomizer--
CLAIM 3, COLUMN 5, LINE 55, change "fluid atomizer" to --fluid-atomizer--
CLAIM 6, COLUMN 6, LINE 6, after "atomizer;" insert --and--

Signed and Sealed this

Twenty-fourth Day of October, 2006

JON W. DUDAS
*Director of the United States Patent and Trademark Office*